(12) United States Patent
Pouletty et al.

(10) Patent No.: US 12,257,040 B2
(45) Date of Patent: Mar. 25, 2025

(54) METHOD AND SYSTEM FOR DETERMINING PROPERTIES IN A VESSEL

(71) Applicant: ARTEDRONE, Paris (FR)

(72) Inventors: Philippe Pouletty, Paris (FR); Maëlle Bruneau, Paris (FR)

(73) Assignee: ARTEDRONE, Paris (FR)

( * ) Notice: Subject to any disclaimer, the term of this patent is extended or adjusted under 35 U.S.C. 154(b) by 387 days.

(21) Appl. No.: 17/636,669

(22) PCT Filed: Aug. 21, 2020

(86) PCT No.: PCT/EP2020/073457
§ 371 (c)(1),
(2) Date: Feb. 18, 2022

(87) PCT Pub. No.: WO2021/032869
PCT Pub. Date: Feb. 25, 2021

(65) Prior Publication Data
US 2022/0280050 A1 Sep. 8, 2022

(30) Foreign Application Priority Data
Aug. 21, 2019 (EP) ..................................... 19315100

(51) Int. Cl.
*A61B 34/20* (2016.01)
*A61B 5/00* (2006.01)
(Continued)

(52) U.S. Cl.
CPC .......... *A61B 5/027* (2013.01); *A61B 5/02007* (2013.01); *A61B 5/02028* (2013.01);
(Continued)

(58) Field of Classification Search
CPC . A61B 5/02007; A61B 5/02028; A61B 34/20; A61B 2034/2055;
(Continued)

(56) References Cited

U.S. PATENT DOCUMENTS

| | | | | |
|---|---|---|---|---|
| 5,419,325 A | * | 5/1995 | Dumoulin | ............ G01R 33/285 600/410 |
| 10,363,012 B2 | | 7/2019 | Browning et al. | |

(Continued)

FOREIGN PATENT DOCUMENTS

JP        2014-000431 A       1/2014

OTHER PUBLICATIONS

International Search Report Corresponding to PCT/EP2020/073457 mailed Oct. 22, 2020.

(Continued)

*Primary Examiner* — Amal Aly Farag
(74) *Attorney, Agent, or Firm* — Finch & Maloney PLLC

(57) ABSTRACT

The invention is directed to a method of determining properties in a vessel or the heart (V) of a patient. It comprises the steps of placing an element in a vessel or the heart(V) and determining a propulsion force (2) acting on the element. Furthermore, at least one of acceleration (3) and velocity (4) of the element is determined. At least one property of a neighbouring medium of the element is determined based on the propulsion force and at least one of acceleration (3) and velocity (4) of the element.

13 Claims, 3 Drawing Sheets

Figure 4:
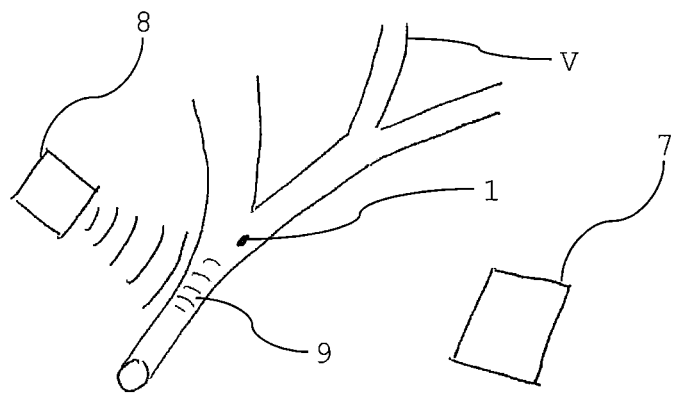

(51) Int. Cl.
*A61B 5/02* (2006.01)
*A61B 5/027* (2006.01)
(52) U.S. Cl.
CPC ............ *A61B 5/6852* (2013.01); *A61B 34/20* (2016.02); *A61B 2034/2055* (2016.02); *A61B 2562/0223* (2013.01)
(58) Field of Classification Search
CPC .......... A61B 2562/0223; A61B 5/6869; A61B 5/6876; A61B 1/041; A61B 1/00158
See application file for complete search history.

(56) References Cited

U.S. PATENT DOCUMENTS

| | | | |
|---|---|---|---|
| 2004/0210128 A1* | 10/2004 | Martel | A61B 34/72 600/411 |
| 2006/0152309 A1 | 7/2006 | Mintchev et al. | |
| 2007/0244520 A1 | 10/2007 | Ferren et al. | |
| 2013/0072789 A1* | 3/2013 | Park | A61B 34/73 335/219 |
| 2014/0155709 A1* | 6/2014 | Ikai | A61B 1/00158 600/302 |
| 2014/0253114 A1 | 9/2014 | Khamesee et al. | |

OTHER PUBLICATIONS

Written Opinion Corresponding to PCT/EP2020/073457 mailed Oct. 22, 2020.
Japanese Office Action Corresponding to 2022-551015 mailed Feb. 20, 2024.
Chinese Office Action Corresponding to 202080056972.6 issued May 20, 2024.

* cited by examiner

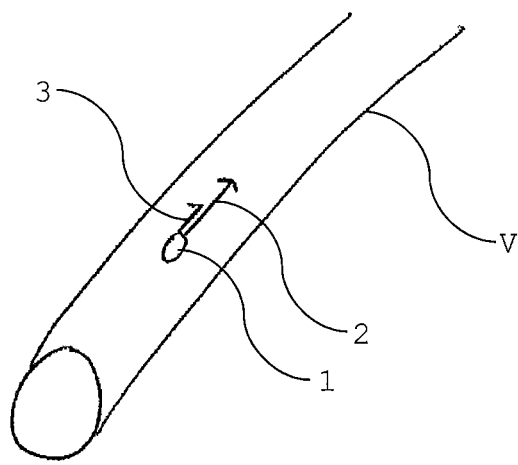
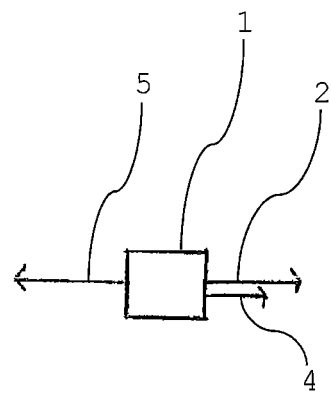
Fig. 1                Fig. 2
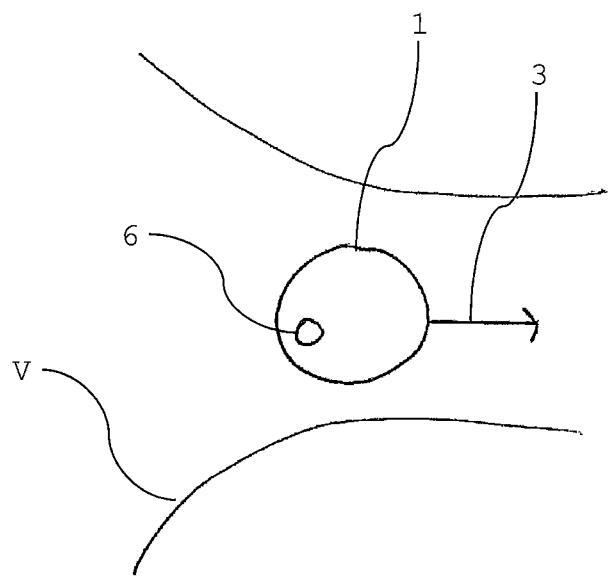
Fig. 3

METHOD AND SYSTEM FOR DETERMINING PROPERTIES IN A VESSEL

The present invention relates to a method and a system for determining properties of tissue or a fluid in a vessel according to the preamble of the independent claims.

It is known in the prior art to treat vessels in a minimally invasive way. For example, implants can be delivered using a catheter device. Such treatments are used e.g. to treat constricted vessels or aneurysms, amongst other conditions. Similarly, microrobots have been used in the prior art to image and/or treat inner parts of a patient's body.

However, a problem that consistently occurs with such devices in both treatments and diagnostic applications is that accurate information about the surrounding of the device is unavailable.

In particular, imaging techniques used in combination with minimally invasive treatments typically only provide limited information about the properties of the surrounding tissue. For example, contrast imaging using X-rays provides anatomic information of the vascular system, but may not be able to provide information on mechanical properties or flow hindrances in the blood stream. Thus, multiple methods are usually necessary in parallel, making the collection of such information slow, costly, and difficult. It is particularly difficult to obtain such information in real time during a treatment with a minimally invasive method.

Thus, the object of the present invention is to overcome the drawbacks of the prior art, in particular to provide a method and a system which allow to determine different properties of tissue or a fluid in a vessel neighbouring a device for treatment or diagnosis of a human body in a simple way.

This and other objects are achieved by the method and the systems according to the characterizing portion of the independent claims of the invention.

The invention relates to a system for determining properties in a vessel or the heart (V) of a patient. The system comprises an element to be placed in a vessel or the heart. The system further comprises means for determining a propulsion force acting on the element, and means for determining at least one of acceleration and velocity of the element. Preferably, the system comprises means for determining both acceleration and velocity of the element.

Such means may in particular comprise a sensor, for example an accelerometer, or a sensor adapted to measure a distance to a reference point inside or outside the patient's body. Additionally or alternatively, the means for determining a propulsion force may also comprise an imaging device and/or a computer to analyse images generated by the imaging device.

Furthermore, the system comprises means for determining at least one property of a neighbouring medium of the element based on the propulsion force, and at least one of acceleration and velocity. For example, such means may comprise a computer, preferably a computer running a software code. Preferably, the means determine at least one property based on both acceleration and velocity of the element.

The method according to the invention provides a way of determining properties in a vessel of a patient. It comprises the steps of:

Placing an element in a vessel or the heart
Determining a propulsion force acting on the element.
Determining at least one of an effective acceleration and effective velocity, in particular both effective acceleration and effective velocity, of the element,
Determining at least one property of a neighbouring medium of the element based on the propulsion force and the at least one of effective acceleration and effective velocity of the element, in particular both of the effective acceleration and effective velocity of the element.

The properties of the vessel that can be determined with the method described herein can be mechanical properties, for example the elasticity, stiffness, ductility, and/or hardness of a tissue. By deduction, it would also be possible to determine anatomical or histological properties of the tissue, in particular the presence of necrotic or cancerous tissue. Of course, it may also be possible to determine physical properties of blood, such as the viscosity and/or flow speed. Additionally or alternatively, the properties can include properties of the vessel influencing the flow, for example obstacles that prevent, slow down or accelerate the flow of blood in the vessel or create turbulences. It is also conceivable that other diagnostically relevant properties are obtained, such as the presence of an aneurysm, a blood clot/thrombus, gas bubbles, and/or a defect in a vessel wall.

A neighbouring medium shall in particular be understood as all biological material in the vicinity of the element that can interact with the element. It can be liquid, solid, gaseous, or comprise a soft material.

An element shall be understood as any device that is adapted to move, at least temporarily, freely inside the human body. It may, in particular, be a microrobot, a sensor, a drug carrier, or a floating element. In particular, the element may comprise a magnetic element, such as a ferromagnetic particle on its inside and/or its surface. It may also consist of a ferromagnetic material.

In particular, the method may be employed only to analyse properties of a vessel. Specifically, the method can be performed for the sole purpose of determining a certain property of interest. As such, the element is only introduced to, and does not serve another purpose than, provide data to perform the method.

Additionally or alternatively, however, it is possible to perform the method with a medical device that is introduced in the body to perform another action as well. For example, a microrobot may be introduced into the body to deliver a drug or treat a target site. The method may then be performed to determine when the microrobot has reached the target site, or even to define the optimal target site.

It would also be conceivable to use a separate element to perform the method in parallel to another treatment.

A propulsion force shall typically and unless otherwise stated be understood as the total force that is exerted on the element in the absence of any interaction with the patient's body. For example, if the element is magnetic and is actuated by a magnetic field, the propulsion force is the force that is exerted on the element by the magnetic field without taking into account blood flow or other forces due to bodily functions, such as friction in the body, blood flow, or blockage from a blood clot. Similarly, if the element comprises a self-propelling means such as a propeller or a jet, the propulsion force would be the force exerted by this self-propelling means. If a combination of a self-propelling means and a magnetic field is used, the propulsion force would include both those forces. It is possible to calculate the theoretical acceleration and velocity from the propulsion force for a given mass of the element.

The effective and theoretical acceleration and velocity will never be the same due to influences such as friction, gravity, drag, and others. In more sophisticated models, such effects may be taken into account.

For example, if some parameters of the tissue or fluid neighbouring the device are known, they are taken into account to calculate a theoretical acceleration or terminal velocity that the element should reach in that tissue based on the propulsion force. For example, if the speed-dependent drag force that the blood exerts on the element is known, the theoretical terminal velocity of the element could be calculated.

By contrast, the effective acceleration and/or effective velocity of the element shall be understood as actual acceleration and/or actual velocity of the element with respect to the patient's body. As such, the difference between the effective acceleration or velocity and the theoretical acceleration or velocity (which can be determined by division of the propulsion force with the mass of the element) provides information on the environment of the element (for example viscosity of the blood) or obstacles.

Consequently, the effective propulsion force shall be understood as the product of the effective acceleration and the mass of the element. For a given element, the effective acceleration is thus an equivalent parameter to the effective propulsion force.

The propulsion force can be measured or determined based on known parameters such as the parameters of an actuator such as a magnetic field acting on the element.

Preferably, the propulsion force is determined based on a sensor comprised in the element. This is particularly advantageous if the exact location of the element is not known or difficult to determine. For example, if the element is located in a large vessel and driven by a magnetic field, the exact properties of the magnetic field at the location of the element may not be known. Thus, if the force exerted on the element by the magnetic field can be measured, this problem is solved.

Additionally or alternatively, it is also conceivable to use another sensor comprised in the element to measure the effective acceleration.

Preferably, the method further comprises the step of imaging an area of a patient where the element is located. In particular, the imaging may be performed using one of X-ray imaging, magnetic resonance imaging (MRI), computer tomography, positron emission tomography (PET), and ultrasound imaging. This can offer several advantages in performing the method. On one hand, if a certain mechanical property is determined by means of the method, imaging data can assist in the correct localisation and interpretation (for example assignment to a certain type of tissue). One the other hand, it is also conceivable to measure the effective acceleration and/or velocity of the element using the imaging data.

Alternatively or additionally, it is also conceivable to use a database of patients for calibration and interpretation of the data for navigation the element or of data gathered by the method according to the invention. In such a database, information about typical patients or groups of patients but also patient individual information might be stored. Calibration and interpretation may also be made by using artificial intelligence methods. In particular, certain information usable for calibration or interpretation may be gathered by deep learning or machine learning methods. Such methods can be carried out during the method according to the invention and/or in preparation thereof.

Alternatively or additionally, it is also conceivable to use data generated by using a first element to modify parameters (e.g. magnetic field) relevant for the navigation for a subsequent element.

Preferably, at least one property of the neighbouring medium is additionally based on the imaging data. For example, imaging data can provide the information whether a certain number of different types of tissue are present. Additionally or alternatively, imaging data may reveal the presence of an obstacle in a vessel. Thus, one property of the neighbouring medium of the element is based on the imaging data, while other properties such as the mechanical properties of the different tissue types or the obstacle. The combination of the imaging data and the mechanical property may allow to conclusively determine what types of tissue are present, and/or what kind of obstacle is in the vessel.

The person skilled in the art will understand that this is merely a non-limiting example of how imaging data can advantageously be used in the method according to the invention. However, it is possible to perform the method without imaging data.

Preferably, the method further comprises the step of determining the location of the element. This provides additional information of where certain tissue types are located in the patient's body. This is particularly advantageous in cases where those tissues are planned to be treated or removed, for example by a surgical technique.

Preferably, the location is determined by means of the imaging technique.

Preferably, the method further comprises a step of saving in a memory the at least one property of the neighbouring medium as a function of the location or time. This allows for analysing multiple locations in a vessel during one session. In particular, the data can subsequently be analysed such as to create one-, two-, or three-dimensional property maps. For example, the stenosis or an aneurysm of a vessel may be determined by means of the method according to invention along the longitudinal axis of said vessel. If the level of stenosis or aneurysm is determined and saved at multiple points, a graph showing the stenosis or aneurysm along the longitudinal axis can be obtained. Similarly, data may also be collected in two or three dimensions.

Preferably, the step of calculating the at least one property of the neighbouring medium is performed by a computer running a software code. This allows for, in particular, automatically performing the method and is thus fast, reliable and cheap.

Preferably, the at least one property of the neighbouring medium is one of mechanical, hemodynamical, anatomical, and histological property. For example, it may be the viscosity of blood, Young's modulus of a tissue, the flow velocity of blood, and/or the size or shape of a vessel, in particular its diameter.

Preferably, the element placed in the vessel comprises a magnetic element and the step of determining the propulsion force comprises determining the field strength of a magnetic field. Determining the field strength shall, in particular encompass the calculation of the properties of the magnetic field at a certain point in space (especially at the location of the element) based on known parameters of a unit generating the magnetic field, but can also comprise measuring the magnetic field at a certain point in space. The measurement of the magnetic field may take place by the element and thus at its location and/or at a reference point.

Preferably, the method further comprises the step of calculating a theoretical acceleration or velocity of the element based on the propulsion force acting on the element.

Preferably, the step of calculating a theoretical value of velocity and acceleration of the element is additionally based on the location of the element and imaging data acquired in the imaging step. For example, the size and blood volume of a vessel may be taken into consideration based on imaging data. Additionally or alternatively, the velocity and pulsatility of the blood flow may be measured and taken into account, in particular by means of Doppler ultrasound imaging. In particular, the location of the element with respect to the vessel wall may also be taken into account.

Preferably, the method further comprises the step of measuring the flow velocity of a liquid, in particular of blood in a vessel or the heart, surrounding the element. Additionally the determination of the at least one property of the neighbouring medium may be based on the flow velocity. In particular, the flow velocity may be determined by means of Doppler ultrasound imaging. However, it is also conceivable to measure the flow velocity with a sensor comprised in and/or on the element.

Preferably, the method further comprises the step of localizing the element by means of at least one detector and/or marker. The marker can be placed on the element and the detector can be placed at a pre-defined location in or with respect to the patient's body. For example, detectors may be placed on the outside of a vessel, on bones such as the skull, or organs such as the heart. Detectors shall be understood as any device adapted to detect or help to detect an element in its vicinity. Markers are associated with the element and help to detect the element, in particular by a sensor.

Detectors may also be adapted to measure the distance to an element. A detector may particularly preferably be an electric sensor, a magnetic sensor or an optical sensor. The markers could be NFC chips, magnets or radiopaque material. Fluorescent or isotopic markers may also be used.

The invention is further directed to a computer program product for analysing the neighbouring medium of an element in a patient's body. It comprises a software code that is adapted to, when run on a computer, perform the step of determining at least one property of a neighbouring medium of the element based on the propulsion force and the at least one of effective acceleration and effective velocity of the element, in particular both of the effective acceleration and effective velocity of the element. The computer program product may in particular be adapted to process imaging data and preferably determine the at least one property of the neighbouring medium based on imaging data of the neighbouring medium acquired by an imaging device. For example, the computer program product may be adapted to determine at least one of velocity and acceleration of an element based on imaging data.

The invention is further directed to a system for determining properties of a vessel. It comprises an element adapted to be carried by and/or actively move in a bodily fluid, a measurement unit, and a calculating unit. The measurement unit is adapted to determine at least one of acceleration and velocity of the element. The calculating unit is adapted to determine at least one property of the vessel based on the at least one of acceleration and velocity of the element. Preferably, at least one of the measurement unit and the calculating unit is adapted to determine a propulsion force acting on the element. For example, the calculating may calculate the propulsion force based on on operating parameter, for example the characteristics of a magnetic field. Additionally or alternatively, the measurement unit may also be adapted to measure a force being exerted on the element, for example by measuring a magnetic field. In particular, the calculating unit may determine the at least property of the vessel by performing a method as described herein, particularly preferably by running a software code that is adapted to perform the steps of a method as described herein.

The person skilled in the art will understand that the system may, in particular, be adapted to perform any of the method steps as described herein.

Preferably, the system comprises an imaging device that is adapted to image an area of a patient's body where the element is located. This, in particular, allows for performing all steps as described in the context of the method according to the invention where an imaging unit can be employed. In particular, the imaging unit may be any one of PET, MRI, ultrasound, X-ray, and CT.

Figure 5:
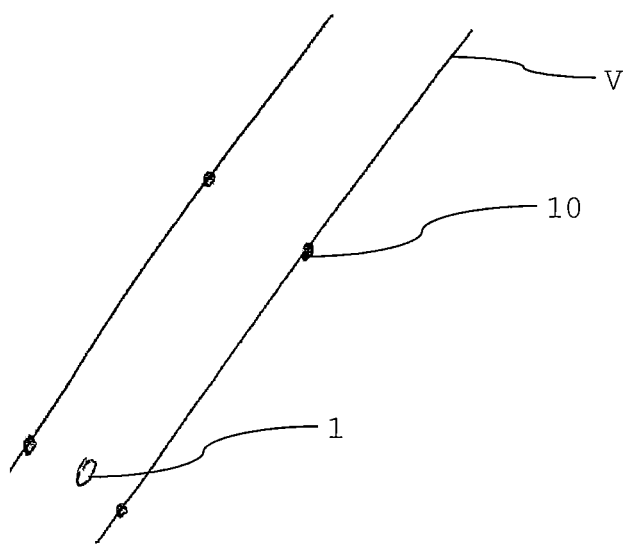
Figure 6:
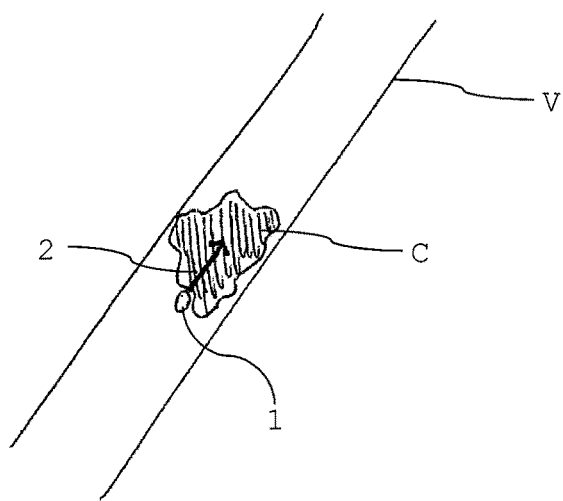
Figure 7:
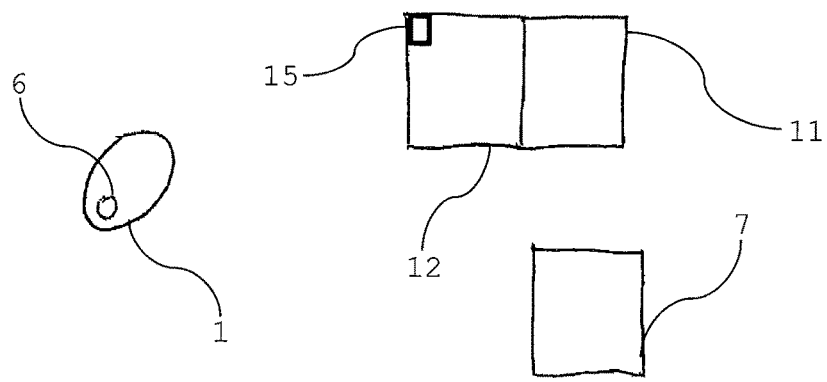
Figure 8:
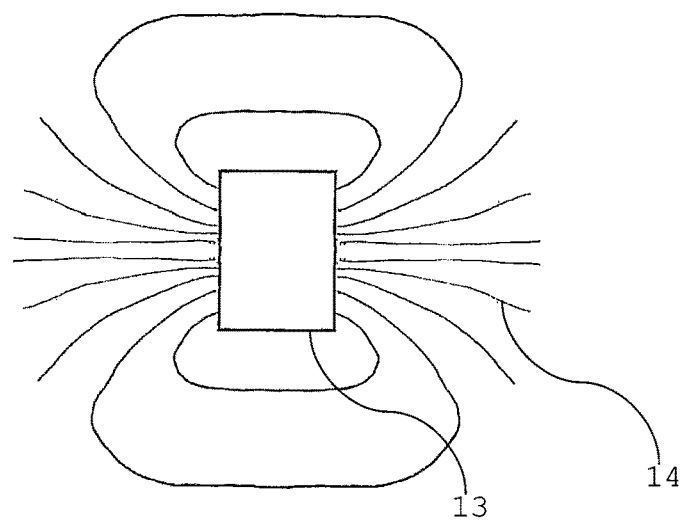

In the following, the invention is described in detail with reference to the following figures, showing:

FIG. 1: schematically an element in a vessel.
FIG. 2: schematically an element with different forces acting on it.
FIG. 3: schematically an element in a narrowing vessel.
FIG. 4: schematically an element in a vessel and imaging devices.
FIG. 5: schematically markers located on a vessel.
FIG. 6: schematically an element in a vessel with a blood clot.
FIG. 7: schematically a system according to the invention.
FIG. 8: schematically a magnetic element.

FIG. 1 shows schematically an element 1 in a vessel V. Here, the element 1 is a moving element comprising a ferromagnetic material. Thus, a magnetic field applied by an external magnet (not shown, see FIG. 8) may guide and/or propel the element 1 inside the vessel V. Thus, it can exert force 2 on the element 1. In this case, in the hypothetical absence of influences e.g. by bodily functions such as blood flow, friction, or gravity, the exerted force 2 by the magnetic field would be the only force acting on the element 1. It thus represents the propulsion force in this example. However, due to fluid resistance, the element is also subject to a drag force. Here, the drag force is unknown and shall be determined in order to determine the fluid properties of blood and the friction on a vessel wall. However, it would also be possible to include fluid resistance and friction in the propulsion force. It is also possible to measure the effective acceleration 3 or velocity 4 of the element. Here, the acceleration 3 is e.g. measured by an accelerometer comprised in the element. Alternatively, it may for example also be measured by means of an imaging device. The effective acceleration 3 represents the difference between the force 2 and the drag force. Thus, it is possible to calculate the drag force and consequently also fluid properties of the blood and the vessel. This is particularly advantageous, of course, where the flow properties of the blood are affected by a condition.

FIG. 2 schematically represents a similar element as shown in FIG. 1. Here, the vessel V is not shown for clarity. In addition, the element has a different shape and has a cubic instead of a quasi-spherical shape. However, it also comprises a ferromagnetic material and can be propelled by a magnetic field. The state schematically shown in FIG. 2 represents an equilibrium state when the element has reached a terminal velocity 4. Hence, the propulsion force 2 and the drag force 5 have equal norm values but opposite signs. The terminal velocity 4 can thus be used to calculate parameters of the blood such as its viscosity. In a similar embodiment of the method, the magnetic field may change its direction with a certain frequency. Instead of measuring the velocity, one may measure the frequency of motion of the element and determine fluid properties of the blood from that.

FIG. 3 shows schematically a different type of element 1. It is spherical and is passively carried by a fluid in the vessel V. It further comprises a sensor that is adapted to measure the effective acceleration 3 of the element 1. Here, the vessel has a constriction causing the flow speed of the blood to temporarily increase. Thus, the accelerometer 6 detects a temporary acceleration (and deceleration in the widening region). Because the element 1 is passively carried in this example, the propulsion force is zero. Hence, the effective acceleration 3 can directly be used to determine properties of the vessel V, in this case the presence of a constriction.

FIG. 4 shows an element 1 carried by a liquid in a vessel V. For clarity, none of the propulsion means are shown in this schematic depiction, but the person skilled in the art will understand that any of the described ways of moving, steering, or guiding the device could be employed in this embodiment. Here, an imaging unit 7 having an X-ray imaging device is employed. The element 1 is visible in X-ray imaging. In addition, the blood contains a contrast agent such that the vessel system is also visible under X-rays. A Doppler imaging unit 8 is employed to visualize the flow 9 of the blood in the vessel system. Of course, the Doppler imaging unit and the X-ray imaging device may be connected to one computer each or to the same computer, for example a computer comprising a computer program product according to the invention for use of the imaging results in the calculation.

FIG. 5 shows an element 1 moving in a vessel V. Here, several detectors 10 are placed around the vessel V. They are formed by closed copper coils around the vessel. The element comprises a permanent magnet that creates a magnetic field around it. Thus, when the element 1 passes a detector 10, the moving magnetic field induces a current in the detector that can be detected. It is also possible to provide an emitting chip on the robot and receivers/detectors placed on the body, that can triangulate the robot position.

FIG. 6 shows another application of the method. Here, the element is moving in a vessel and is propelled by a magnetic field that exerts a force 2 on the element 1 via a ferromagnetic element comprised in it. However, a blood clot C has formed in the vessel V and blocks or restricts the blood flow. Consequently, the element 1 stops moving as well once it hits the blood clot C. Thus, the effective velocity of the element becomes zero, while the propulsion force 2 is non-zero. This allows for the determination of a property, in this case the presence of a blood clot. Of course, it would also be conceivable to additionally measure the effective acceleration of the element 1 which would additionally give information about the location of the blood clot C and/or its mechanical properties (a softer clot C would lead to lower negative acceleration values).

FIG. 7 shows schematically a system according to the invention. It comprises an element 1, in which a sensor 6 is arranged. The sensor shown here is adapted to measure acceleration of the element and, optionally, basic values such as temperature and pressure. The system further comprises a measurement unit 11 and an analyser unit 12. The measurement unit is in particular adapted to receive acceleration values from the sensor. However, it may also measure values based on markers or detectors 10. Although not required to perform the method, in certain embodiments it may be advantageous to measure the effective propulsion force acting on the element 1. Thus, in this non-limiting example, the measurement unit 11 is also adapted to measure a magnetic field at the location of the element, in particular by interaction with the sensor 6. The analyser unit 12 is adapted to process the values received from and by the measurement unit 11. In addition, it comprises a memory 15 to save values. For example, it may receive an effective acceleration value from the sensor 6 comprised in the element 1. In addition, the propulsion force may be known from the parameters of an external magnetic unit (see FIG. 8) or be measured by the sensor 6. In any case, the analyser unit is adapted to process these values and analyze them to determine at least one property of the vessel. The property value can optionally be saved in the memory 15. It would be conceivable to combine the system with a display adapted to show data, in particular two-dimensional and/or three-dimensional illustrations of data such as a reconstruction of the anatomy of a patient, based on the values saved in the memory. It will be understood that any of the examples and embodiments described herein may be realized with this system.

FIG. 8 shows a magnetic element 14 that may be used to propel the element 1. Here, it comprises an electromagnet that can selectively be turned on and off to create a magnetic field 14. Of course, a permanent magnet may also be employed. It would also be conceivable to use electric energy to operate an impeller, a propeller, or another propulsion means.

The invention claimed is:

1. A system for determining properties in a vessel or a heart of a patient, comprising:
   a magnetic element to be placed in the vessel or the heart and adapted for being actuated by a magnetic field,
   means for determining a magnetic propulsion force acting on the magnetic element when actuated by the magnetic field,
   an imaging device adapted for imaging an area surrounding the magnetic element and allowing to determine the location of the magnetic element with respect to the anatomy,
   means for determining at least one of an effective acceleration and effective velocity based on imaging data obtained by the imaging device,
   means for determining at least one property of a tissue of the magnetic element, based on a difference between a theoretical acceleration or terminal velocity calculated determined based on the magnetic propulsion force, and at least one of the effective acceleration and the effective velocity of the magnetic element,
   the property being selected from an elasticity, stiffness, ductility, and hardness.

2. A method for determining properties in a vessel or a heart of a patient, comprising the steps:
   placing a magnetic element adapted for being actuated by a magnetic field in the vessel or the heart
   determining a magnetic propulsion force acting on the magnetic element by the magnetic field,
   determining at least one of an effective acceleration and an effective velocity of the magnetic element based on imaging data,
   determining at least one property of a neighbouring tissue of the magnetic element based on a difference between a theoretical acceleration or terminal velocity calculated based on the magnetic propulsion force, and
   at least one of the effective acceleration and the effective velocity of the magnetic element,
   the property being selected from a elasticity, stiffness, ductility, and/or and hardness.

3. The method according to claim 2, wherein the propulsion force is measured by a sensor comprised in the magnetic element.

4. The method according to claim 2, further comprising the step of imaging an area of a patient where the magnetic element is located.

5. The method according to claim 2, further comprising the step of determining the location of the magnetic element.

6. The method according to claim 4, further comprising the step of determining the location of the magnetic element.

7. The method according to claim 5, further comprising the step of saving in a memory the at least one property of the neighbouring tissue as a function of the location or time.

8. The method according to claim 2, wherein the step of calculating the at least one property of the neighbouring tissue is performed by a computer running a software code.

9. The method according to claim 2, wherein the at least one property of the neighbouring tissue is one of a mechanical, hemodynamical, anatomical, and histological property.

10. The method according to claim 2, wherein the step of determining the propulsion force comprises determining of the field strength of a magnetic field.

11. The method according to claim 4, wherein the step of determining the propulsion force comprises determining of the field strength of a magnetic field.

12. The method according to claim 2, further comprising the step of measuring the flow velocity of a liquid surrounding the magnetic element and additionally base the determination of the at least one property of the neighbouring tissue on the flow velocity.

13. The method according to claim 2, further comprising the step of localizing the element by means of at least one detector or marker placed on the element or at a pre-defined location in the patient's body.

* * * * *